(12) United States Patent
Legerton

(10) Patent No.: US 7,891,810 B2
(45) Date of Patent: Feb. 22, 2011

(54) MULTIFOCAL CONTACT LENS

(75) Inventor: Jerome Legerton, San Diego, CA (US)

(73) Assignee: Liguori Management, San Diego, CA (US)

(*) Notice: Subject to any disclaimer, the term of this patent is extended or adjusted under 35 U.S.C. 154(b) by 117 days.

(21) Appl. No.: 12/429,113

(22) Filed: Apr. 23, 2009

(65) Prior Publication Data
US 2010/0271596 A1 Oct. 28, 2010

(51) Int. Cl.
G02C 7/04 (2006.01)
G02C 7/02 (2006.01)

(52) U.S. Cl. .................. 351/161; 351/160 R; 351/177

(58) Field of Classification Search ............ 351/160 R, 351/160 H, 177, 161
See application file for complete search history.

(56) References Cited

U.S. PATENT DOCUMENTS

| | | | |
|---|---|---|---|
| 3,684,357 A | 8/1972 | Tsuetaki | |
| 4,943,150 A | 7/1990 | Deichert et al. | |
| 5,450,145 A | 9/1995 | Valentine | |
| 5,570,142 A | 10/1996 | Lieberman | |
| 5,574,518 A * | 11/1996 | Mercure | 351/161 |
| 5,790,235 A | 8/1998 | Kirschbaum | |
| 6,076,930 A * | 6/2000 | Malchow et al. | 351/247 |
| 6,491,393 B1 | 12/2002 | Appleton | |
| 7,281,795 B2 * | 10/2007 | Sandstedt et al. | 351/161 |
| 7,431,455 B2 | 10/2008 | Chernyak | |
| 7,695,136 B2 * | 4/2010 | Dai | 351/177 |
| 2005/0280777 A1 | 12/2005 | Dai | |
| 2006/0023162 A1 | 2/2006 | Azar et al. | |

FOREIGN PATENT DOCUMENTS

EP 0 445 994 9/1991

* cited by examiner

*Primary Examiner*—Jordan M. Schwartz
(74) *Attorney, Agent, or Firm*—Sheppard Mullin Ritcher & Hampton LLP; David E. Heisey

(57) ABSTRACT

The present invention provides a multifocal contact lens comprising a central contact lens area having a size, a position, and an optical power; an outer contact lens area having a size, a position, and an optical power; wherein the size, the position, and the optical power of the central contact lens area and the outer contact lens area are determined according to a measurement of the size of the pupil under a first light condition, a measurement of the reactivity of the pupil under a varying light condition or a varying focal demand, and a measurement of movement of the pupil under a varying light condition or a varying focal demand.

22 Claims, 6 Drawing Sheets

MULTIFOCAL CONTACT LENS

TECHNICAL FIELD

The present invention relates generally to contact lenses, and more particularly, some embodiments relate to multifocal contact lenses.

DESCRIPTION OF THE RELATED ART

Multifocal contact lenses are sometimes used in the treatment of presbyopia. Such lenses typically have a first area with an optical power configured to correct the vision of the patient when focusing on near objects, and a second area with an optical power configured to correct the vision when focusing on far objects. In these lenses, the placement and size of the areas is typically determined according to populational statistics or physiological generalities.

BRIEF SUMMARY OF EMBODIMENTS OF THE INVENTION

According to an embodiment of the invention, a multifocal contact lens, comprises a central contact lens area having a size, a position, and an optical power; an outer contact lens area having a size, a position, and an optical power; wherein the size, the position, and the optical power of the central contact lens area and the outer contact lens area are determined according to a measurement of the size of the pupil under a first light condition, a measurement of the reactivity of the pupil under a varying light condition or a varying focal demand, and a measurement of movement of the pupil under a varying light condition or a varying focal demand. As used herein, the term "central contact lens area" means an inner contact lens area with at least some portions located within the outer contact lens area;

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

The present invention is directed toward a multifocal contact lens and a method for prescribing the same. In one embodiment, a contact lens is provided having an outer area and a central area, wherein the areas' sizes, shapes, positions, and optical powers are determined according to measurements made of a patient's eye under a variety of lighting conditions and focal demands.

Figure 1:
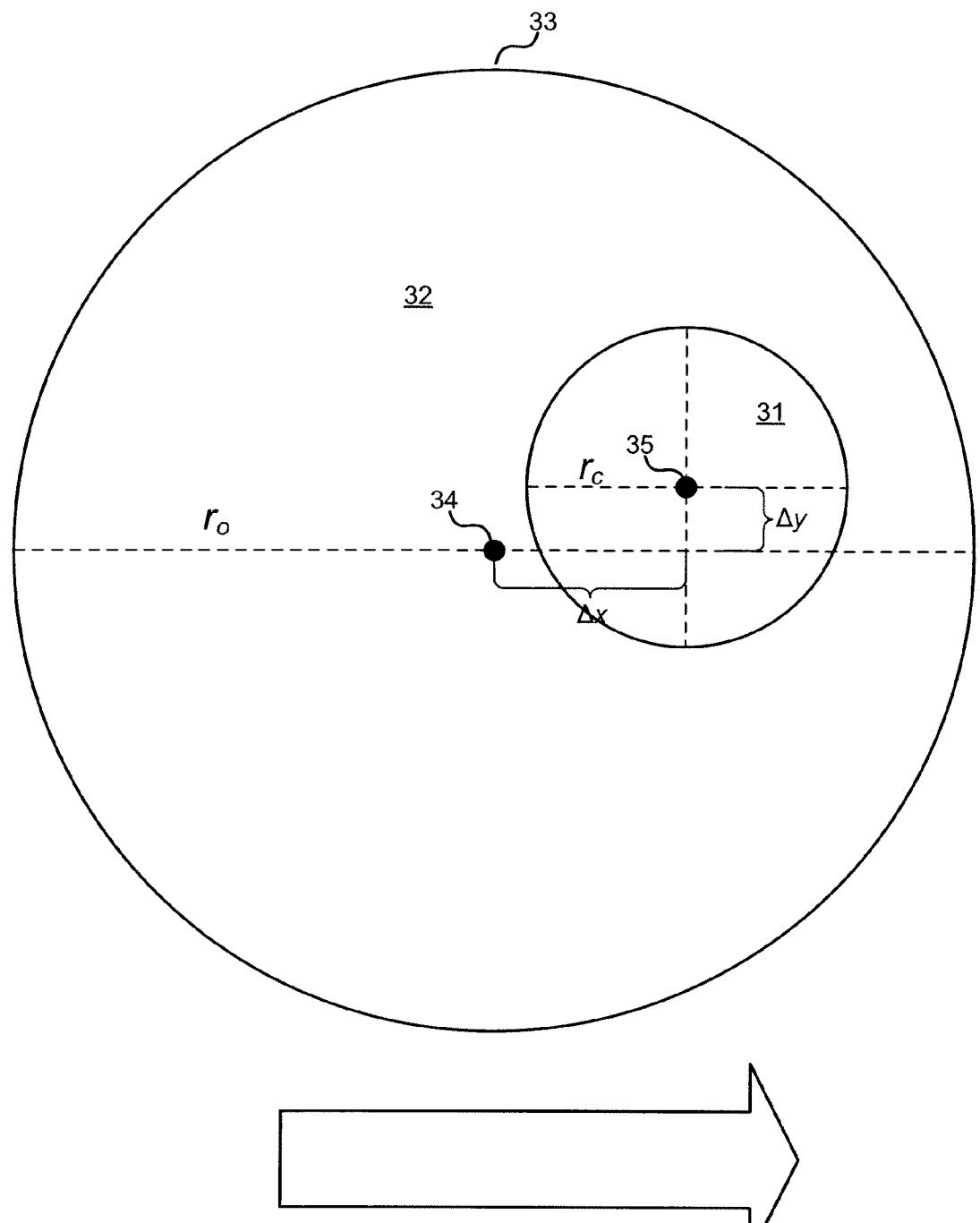
FIG. 1 illustrates a multifocal contact lens according to an embodiment of the invention.

FIG. 1 illustrates a multifocal contact lens according to an embodiment of the invention. As indicated by the arrow, the contact lens of FIG. 1 is a right eye lens. Contact lens 33 comprises an outer area 32 and a central area 31. In this embodiment, one of the areas is configured to correct a presbyopic patient's vision when the patient's pupil is in a first orientation, and the other area is configured to treat the patient's vision when the pupil is in a second orientation. In the illustrated example, central area 31 comprises a circle and outer area 32 comprises a circle with the central circle omitted. Accordingly, (a) the position of the central area ($\Delta x$, $\Delta y$), here measured as a displacement or translation of the central area's center 35 from the outer area's center 34, (b) the radius of the central area $r_c$, and (c) the radius of the outer area $r_o$ are configured according to measurements of the patient's pupil.

Figure 2A:
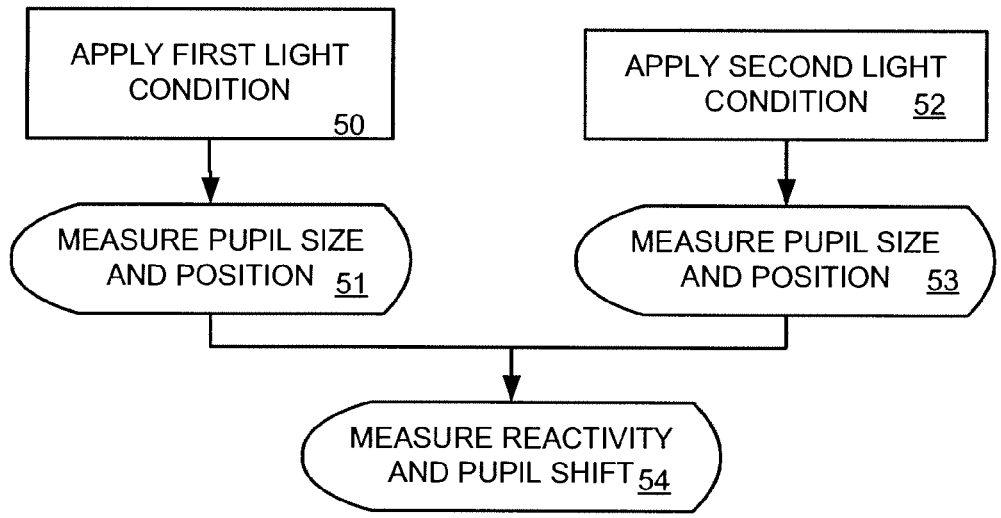
FIG. 2A illustrates a method of determining a pupil's response to changing light conditions according to an embodiment of the invention.

FIG. 2 illustrates a variety of such measurements that may be used in various embodiments of the invention. More particularly, FIG. 2A illustrates a method of determining a pupil's response to changing light conditions according to an embodiment of the invention. In step 50, a pupil is measured under a first lighting condition, such as under a scotopic illumination level. After the pupil has adjusted to this lighting condition, the pupil's size and position 51 are measured. In step 52, the pupil is measured under a second lighting condition, such as a photopic illumination level. After the pupil has adjusted to this new lighting condition, the pupil size and position under the new condition 53 are measured. Comparison of the measurements allows the reactivity of the pupil and the pupil shift to be determined. For example, the reactivity of a patient's pupil may be determined by comparing the size of the pupil under a scotopic illumination level to the size and pupil under a photopic illumination level, where the two illumination levels are determined according to the levels of illumination that would normally be encountered by the patient.

In other embodiments, the reactivity of the pupil may be determined more dynamically by applying a plurality of discrete illumination levels, or by continuously varying the first light condition to reach the second light condition. For example, such a procedure might comprise measuring the size of the pupil under a common scotopic illumination level and slowly increasing the illumination level until it reaches a common photopic illumination level. Accordingly, nonlinear responses of the pupil to changing light levels may be measured and determined. For example, a specific patient's pupil might be more reactive within the mesopic range of illumination, and this may be accommodated for in the configuration of the contact lenses. Similarly, pupil shift during similar procedures may be measured.

Figure 2B:
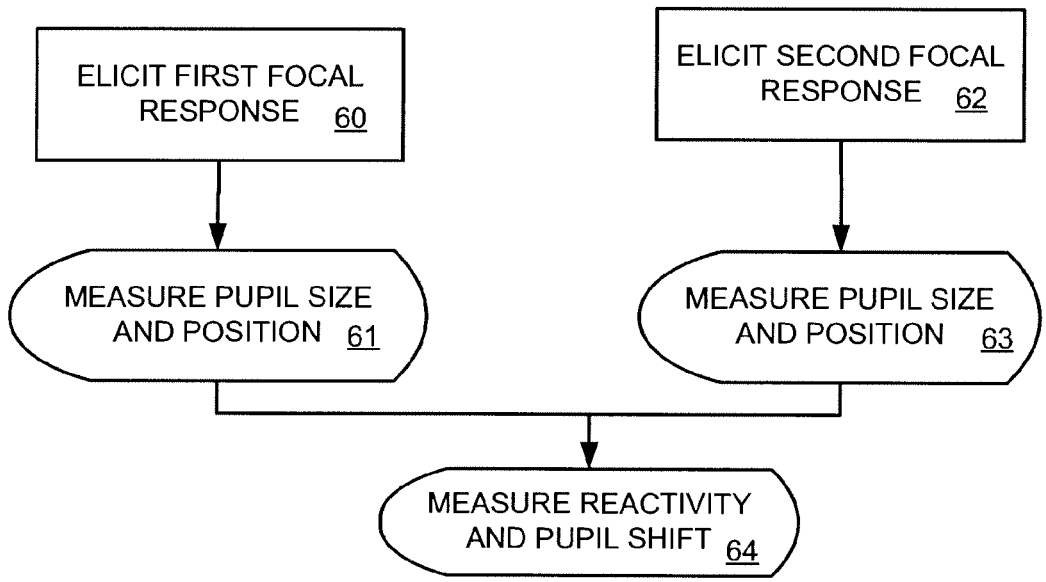
FIG. 2B illustrates methods of determining a pupil's characteristics under varying focal demands according to an embodiment of the invention.

FIG. 2B illustrates methods of determining a pupil's characteristics under varying focal demands according to an embodiment of the invention. In step 60, a first focal response is elicited. For example, an object such as a test chart may be presented to the patient at a first distance, such as a typical reading distance. Accordingly, the pupil size and position 61 may be measured as the patient focuses on objects, such as words, on the test chart. In step 62, a second focal response is elicited. For example, an object may be placed at a point to allow the response of a patient's pupil under far distance viewing to be measured 63. By comparing the results of these measurements, the reactivity of the pupil and the pupil shift in response to changing focal demands may be measured.

Figure 2C:
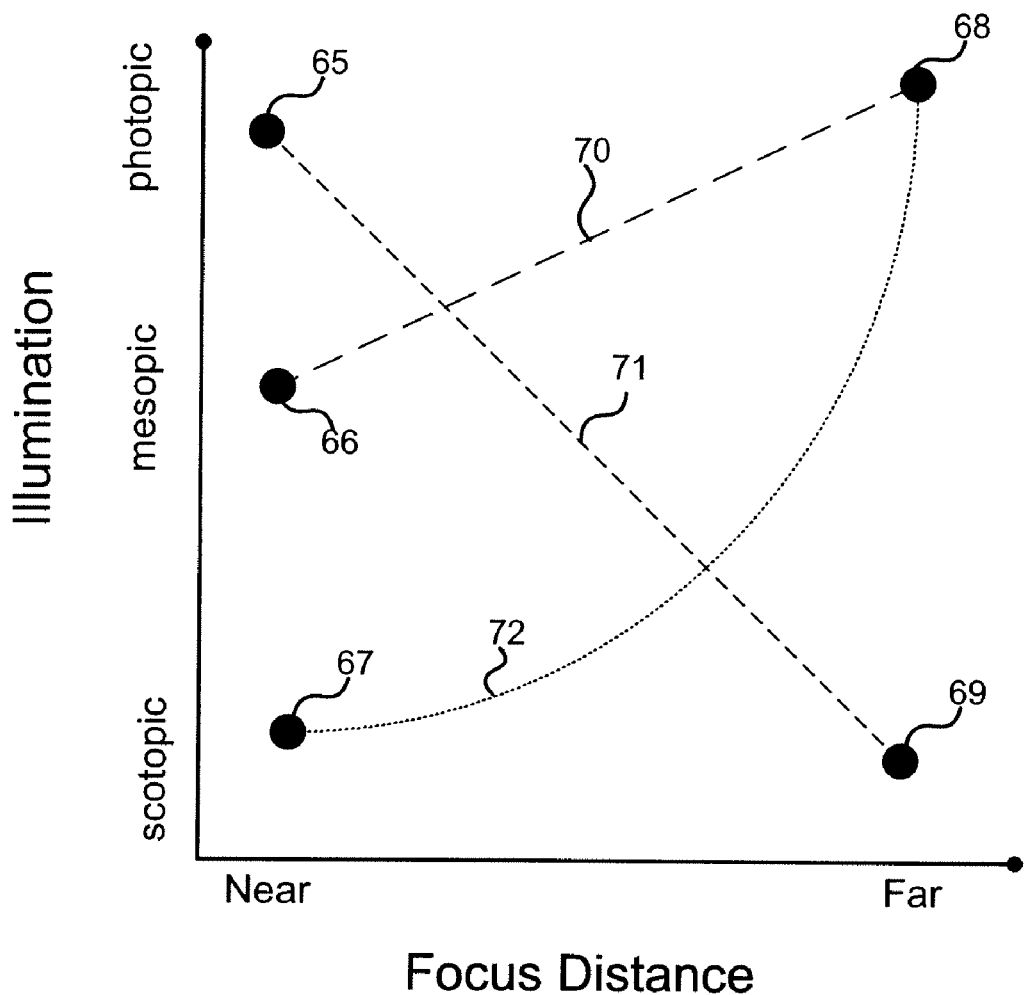
FIG. 2C illustrates methods of determining pupil characteristics under varying light and focal conditions according to an embodiment of the invention.

As described herein, multifocal contact lenses may be developed according to patient specific measurements taken under a variety of optical conditions FIG. 2C illustrates a few such measurement paths according to various embodiments of the invention. Measurement path 71 illustrates the situation where a pupil is measured when a patient is presented with a near object under photopic conditions at point 65. In path 71, the patient is presented with objects that are farther away under gradually decreasing illumination conditions until the patient is presented with an object at the farthest distance, such as infinity, under scotopic illumination conditions at point 69. Measurement path 70 illustrates the case of providing a patient with a plurality of other illuminations and focal requirements between a near object under a mesopic illumination conditions, at point 66, and a far object under photopic illumination conditions, at point 68.

In some embodiments, pupil measurements may be taken at points 65 and 69 and at any other point along a measurement path or may be taken continuously along the entire path. Accordingly in these embodiments, nonlinear pupil responses according to varying conditions may be determined. In further embodiments, the illumination level and focal distance presented along a measurement path are not linearly dependent, such as a random walk between two points. For example, measurement path 72 illustrates a curved path between a scotopic near condition at point 67 and a photopic far condition at point 68. In some embodiments, patients may be measured along a plurality of paths to determine a general pupil profile as a function of illumination and focal distance. In other embodiments, predetermined paths may be configured according to the visual conditions a particular patient is likely to encounter. For example, an architect may spend the majority of his near focal activities at a draft table and the majority of his far focal activities outside in bright daylight. Accordingly, the architect's pupil may be evaluated under conditions similar to measurement path 70.

With reference again to FIG. 1, some embodiments of the invention allow multifocal contact lenses to be developed for patients according to measurements of the characteristics of the patient's pupil, for example as discussed with respect to FIG. 2. In some embodiments, if the pupil is larger than a predetermined size value and less reactive than a predetermined reactivity value, then the optical power of the central area is configured to correct a patient's distance vision; and if the pupil is smaller than the predetermined size value and more reactive than a predetermined reactivity value, then the optical power of the central area is configured to correct a patient's near vision. Correspondingly, if the pupil is larger than the predetermined size and less reactive than the predetermined reactivity, then the optical power of the outer area is configured to correct a patient's near vision; and if the pupil is smaller than the predetermined size and more reactive than the predetermined reactivity, then the optical power of the outer area is configured to correct the patient's far vision.

In some embodiments, the predetermined size value may comprise an average value of pupil size of a patient's peer population, or may comprise a modification of this value. For example, in one embodiment the predetermined size value might comprise 90% of the average pupil size of the patient's peer population. Likewise, in these embodiments, the predetermined reactivity value may comprise an average reactivity of the patient's peer population, or a modification thereof. For instance, in the example embodiment the predetermined reactivity value might comprise 90% of the average reactivity value of the patient's peer population. Accordingly, if a patient's pupil was 110% larger than the average pupil size and 85% as reactive, the patient's multifocal contact lenses would have central areas configured to correct the patient's far vision and outer areas configured to correct the patient's near vision.

In further embodiments, the size of the central and outer areas may be configured according to these patient measurements. For example, an algorithm may be employed to determine an appropriate size of the central and outer areas corresponding to a desired optical performance. For example, in the illustrated embodiment in FIG. 1, the radius of the central area may be determined according to an algorithm that assigns weights to various desired characteristics. For example, a patient having a smaller than average pupil size and a greater than average reactivity may have an occupation requiring the patient to view a computer screen for the majority of the contact wearing time. Accordingly, this patient may be fitted with a contact lens having a central area configured to correct near distance viewing and an outer area configured to correct far distance viewing. Further, because the patient's computer screen is likely bright enough to provide photopic illumination, the weighting function may involve assigning a 90% weight to the size of the patient's pupil under photopic and near viewing conditions and assigning a 10% weight to the size of the patient's pupil under scotopic illumination. In this example, the size of the central area would be $0.9 \times S_p + 0.1 \times S_s$ where $S_p$ is the size of the pupil under photopic illumination and $S_s$ is the size of the pupil under scotopic illumination.

In further embodiments, the position of the two areas may be configured according to measurements of the patient's pupil characteristics. In some embodiments, this comprises adjusting the position of the central area according to measurements of the patient's pupil shift during typical tasks. For example, if the majority of a patient's reading is done on a computer screen, measurements of the pupil shift may be taken under scotopic illumination conditions, wherein the viewing reference is placed at, or slightly above, the midline of the eye to mimic computer screen viewing conditions. As another example, if the majority of the patient's reading is done off of paper, measurements of the pupil shift may be taken under mesopic illumination conditions, wherein the viewing reference is placed at or slightly below the midline of the eye to mimic paper reading conditions. Accordingly, the areas of the contact lens may be positioned such that the central area is aligned with the eye's visual axis and pupil under a first viewing condition and the outer area is aligned with the eyes visual axis and pupil under a second viewing condition.

Still further embodiments may incorporate further measurements into the lens configuration. For instance, the position and size of the lens areas may be configured according to rotational and translational stability of a test contact lens worn on the patient's eye. For example, a patient whose near viewing mostly occurs while reading papers may have a near gaze that is relatively inferior and medial, and this gaze may be more translationally instable than a relatively superior and medial gaze of a patient whose near viewing mostly occurs on a computer. Accordingly, the configurations of the lenses of these two patients may vary according to the difference in the predictability of the lens position on the eye. For example, a weighting factor towards a larger near viewing area may be provided for the inferior gazing patient to accommodate for sliding movements of the lens on the eye. Similarly, differences in the rotational stability of various patients may be accounted for in the lens configuration. Other such measurements and algorithms may consider effects such as the patient's age, emotional states, fatigue, and the effects of chemical agents administered to the eye or by way of the bloodstream.

Figure 3:
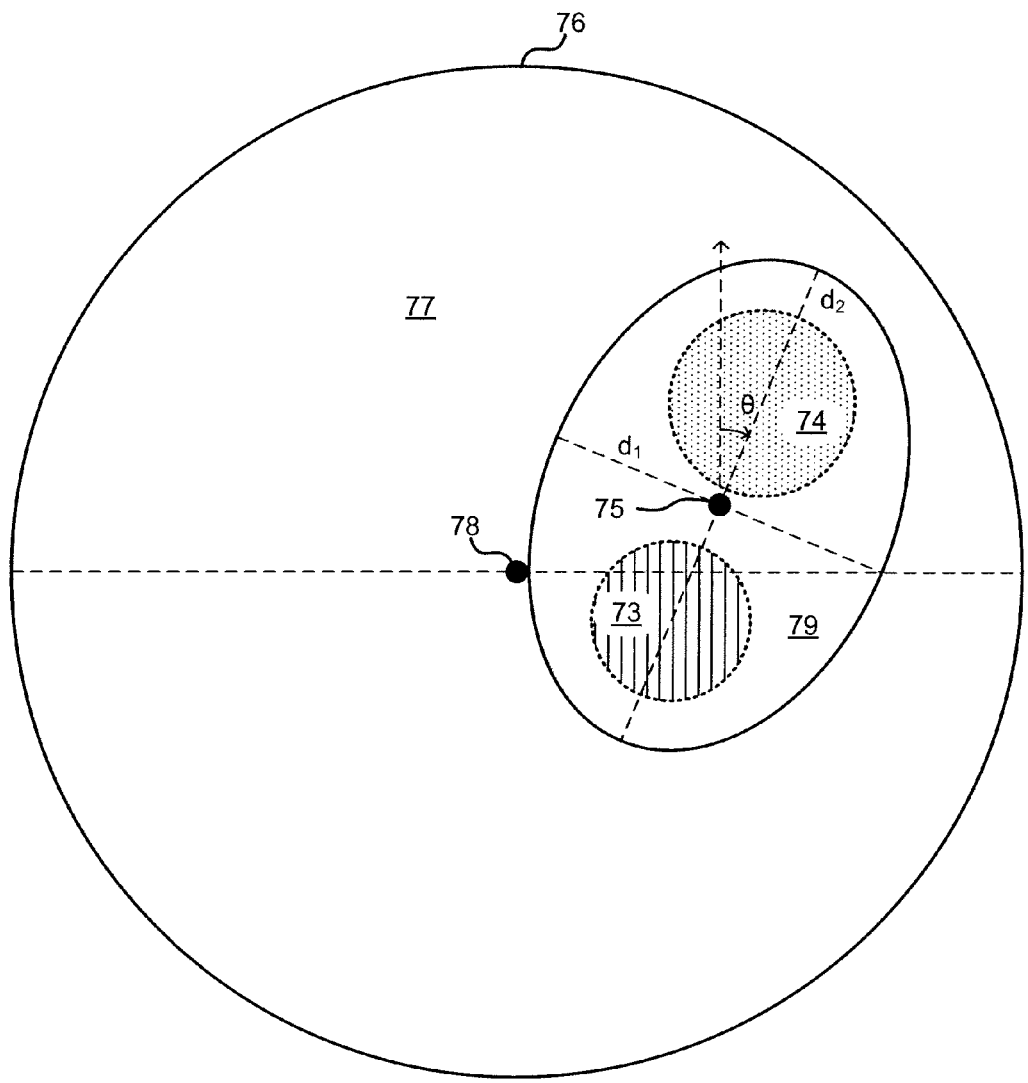
FIG. 3 illustrates a multifocal contact lens having an asymmetrical central area according to an embodiment of the invention.

FIG. 3 illustrates a multifocal contact lens having an asymmetrical central area according to an embodiment of the invention. As with the contact lens illustrated in FIG. 1, the central area 79 of contact lens 76 may be displaced from the center 78 of the contact lens 76. In some embodiments, central area 79 may be rotationally asymmetrical. In the illustrated embodiment, central area 79 is an ellipse having a semi-minor axis $d_1$, a semi-major axis $d_2$, and a rotation of $\theta$ with respect to the superior-inferior axis. For example, such a central area might be prescribed if the patient spends a large amount of time under different viewing conditions. For example, if a patient divides his time between viewing papers and a computer, central area 79 may be configured such that it provides near viewing correction when the pupil and visual axis is aligned with area 73 and when the pupil and visual axis is aligned with area 74.

Figure 4:
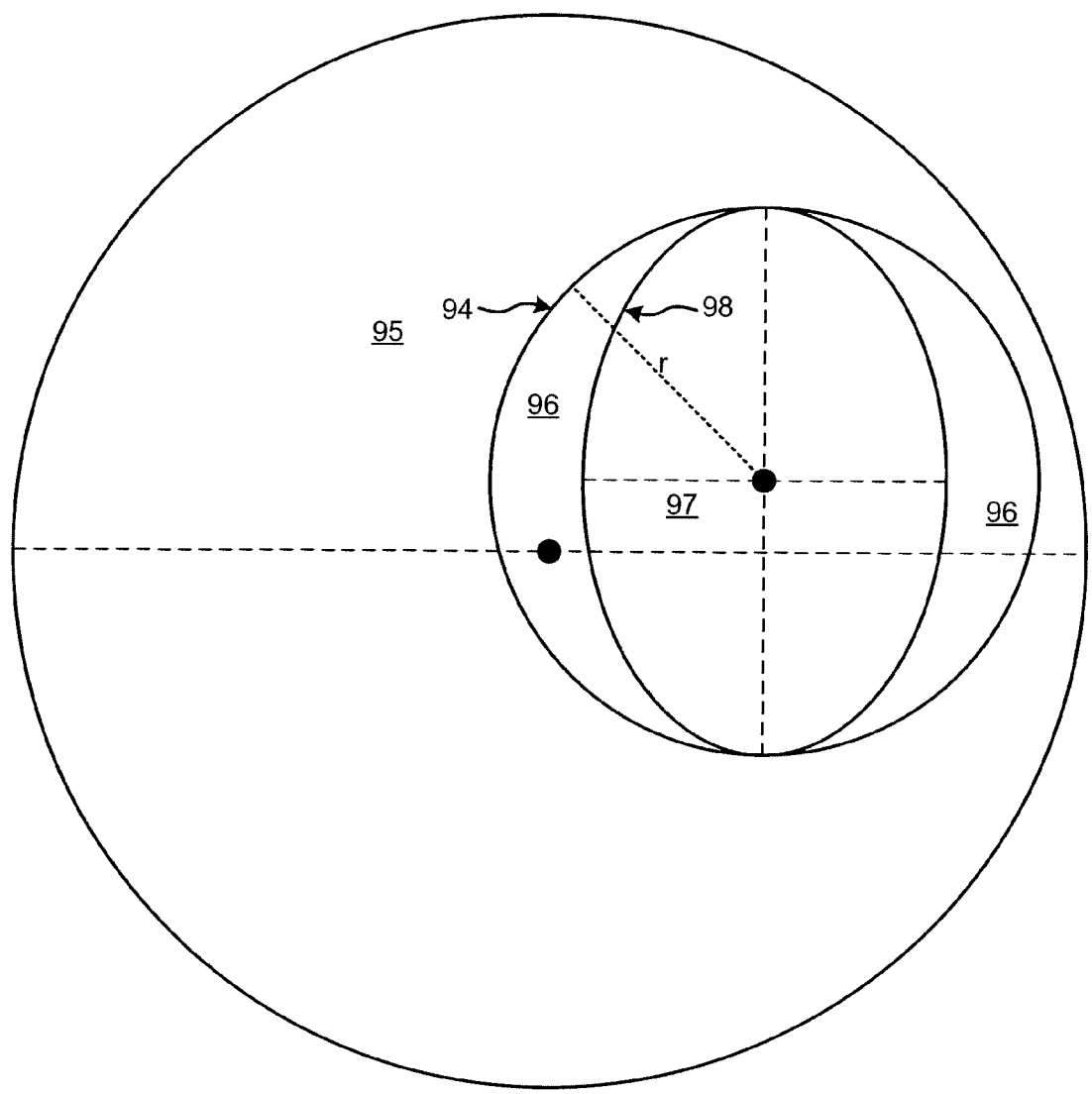
FIG. 4 illustrates a multifocal contact lens having an asymmetrical central area and a constant radius transition zone according to an embodiment of the invention.

FIG. 4 illustrates a multifocal contact lens having an asymmetrical central area and a transition zone according to an embodiment of the invention. In some embodiments with rotationally asymmetric central areas, such as embodiments employing non-toric lenses, there may be a vertical profile difference between the boundary of the central area and the boundary of the outer area at the border between the central and outer areas. Accordingly, a transition zone 96 may be provided to reconcile profile differences between a central area 97 and an outer area 95.

In the embodiment illustrated in FIG. 4, the transition zone 96 has a dual crescent shape such that the area covered by the transition zone 96 combined with the central zone 97 forms a circle with radius r. Such a transition zone may be characterized by a height function defined within the zone under the constraints that the height function has the same profile as central area 97 on contour 98 and has the same profile as outer area 95 on contour 94. Various height profiles may be used in conjunction with such boundary conditions. For example, transition zone 96 may have a linear, non-curved, profile providing a constant height gradient between the profiles of central zone 97 and outer zone 95. In further embodiments, transition zone 96 may have a profile configured to reduce, or eliminate, visual noise or interference caused by the profile differences. For example, the transition zone 96 may be described by a conic constant that varies in two or more meridians, or a polynomial that varies in two or more meridians.

Figure 5:
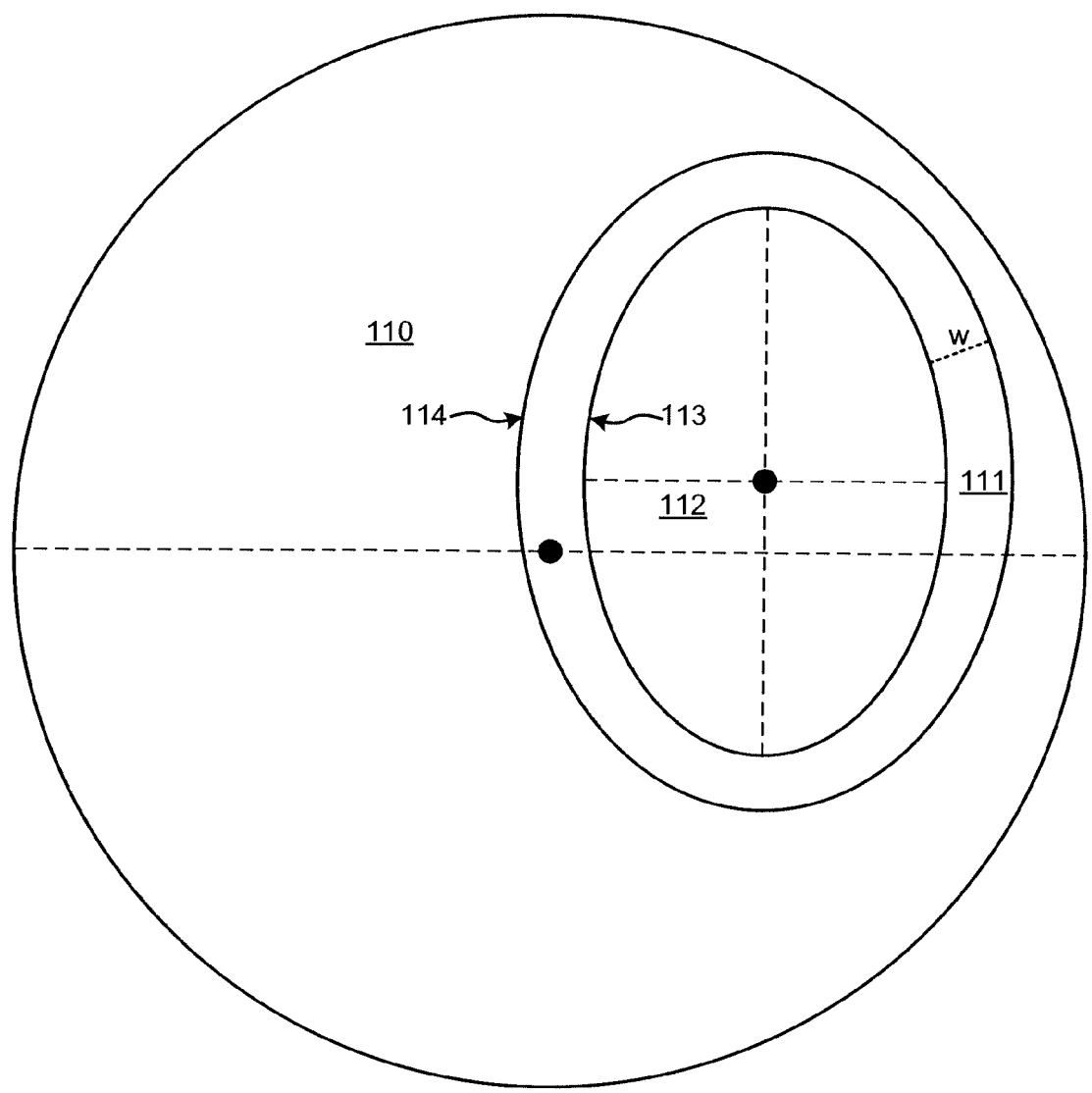
FIG. 5 illustrates a multifocal contact lens having an asymmetrical central area and a constant width transition zone according to an embodiment of the invention.

FIG. 5 illustrates a multifocal contact lens having an asymmetrical central area and a transition zone having a constant width according to an embodiment of the invention. As described with respect to FIG. 4, a transition zone 111 may be characterized by a height profile under the restrictions that the inner boundary 113 smoothly join with the outer perimeter profile of central zone 112 and that outer boundary 114 smoothly join with the profile of outer zone 110. In this embodiment, rather than being configured to provide a substantially circular central portion, transition zone 111 is configured to have a constant width throughout the circumference of the central zone 112. Transition zone 111 may be configured to have any predetermined height profile, such as a non-curved, linear profile, a profile described by a conic constant that varies in two or more meridians, or a polynomial that varies in two or more meridians.

In these embodiments, various materials and optical lens configurations may be used. For example, the entire lens may comprise (a) a soft lens material such as a hydrogel polymer, or silicone hydrogen material; (b) a rigid lens materials such as a rigid gas permeable lens material; or (c) the lens may be a hybrid design where one of the areas comprises a soft lens material and the other comprises a rigid lens material. These lenses may be further equipped with various types of optics. For example, the central or outer area may comprise (a) spherical optics; (b) aspherical optics; (c) toric optics; (d) diffractive optics, (e) apertures to extend the depth of focus, or (f) electronicly modulated pixel optics wherein the index of refraction is varied to produce multifocality. In some embodiments, the multifocal contact lens as described herein may be configured such that each of the patient's eyes is provided an equivalent bilaterally symmetric lens. For example, a patient having a larger and less reactive than average pupil may be provided lenses where the lens for each eye comprises a central area configured for distance viewing and an outer area configured for near viewing. In other embodiments, the lenses may be bilaterally asymmetric. For example, a patient having a larger but more reactive than average pupil may be provided a lens on one eye with an outer area configured for near viewing and an inner area configured for distance viewing, while the other eye is provided a lens with an outer area configured for distance viewing and an inner area configured for near viewing.

While various embodiments of the present invention have been described above, it should be understood that they have been presented by way of example only, and not of limitation. Likewise, the various diagrams may depict an example architectural or other configuration for the invention, which is provided to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional configurations can be implemented to implement the desired features of the present invention. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A multifocal contact lens, comprising:
    a central contact lens area having a size, a position, and a first optical power;
    an outer contact lens area having a size, a position, and a second optical power, the second optical power differing from the first optical power;
    wherein the size, the position, and the optical power of the central contact lens area and the outer contact lens area are determined according to a measurement of the size of the pupil under a first light condition, a measurement of the reactivity of the pupil under a varying light condition or a varying focal demand, and a measurement of movement of the pupil under a varying light condition or a varying focal demand.

2. The contact lens of claim 1, wherein:
    the size of the pupil is less than a predetermined size value and the reactivity of the pupil is greater than a predetermined reactivity value; and
    the optical power of the central area is configured to improve near vision and the optical power of the outer area is configured to improve far vision.

3. The contact lens of claim 1, wherein:
    the size of the pupil is greater than a predetermined size value and the reactivity of the pupil is less than a predetermined reactivity value; and
    the optical power of the central area is configured to improve far vision and the optical power of the outer area is configured to improve near vision.

4. The contact lens claim 1, wherein the central area is positioned away from a center of the contact lens, wherein the distance from the central area to the center is configured according to the movement of the pupil.

5. The contact lens of claim 1, wherein the central area is spherical or diffractive.

6. The contact lens of claim 1, wherein the central area is rotationally asymmetric.

7. The contact lens of claim 1, wherein the contact lens is a rigid lens.

8. The contact lens of claim 1, wherein the central area is rigid and the outer area is soft, or the central area is soft and the outer area is rigid.

9. A method for prescribing a contact lens, comprising:
    measuring the size of a pupil under a first light condition;
    measuring the reactivity of the pupil under a varying light condition or a varying focal demand;
    measuring a movement of the pupil under a varying light conditions or a varying focal demand; and
    determining a size and a position of a central contact lens area having a first optical power and a size and a position of an outer contact lens area having a second optical power according to the measurements, and the second optical power differing from the first optical power;
    wherein the outer lens area substantially surrounds the central lens area.

10. The method of claim 9, further comprising determining an optical power of the central area to improve near vision and an optical power of the outer area to improve far vision when the pupil size is less than a predetermined size value and the pupil reactivity is greater than a predetermined reactivity value.

11. The method of claim 9, further comprising determining an optical power of the central area to improve far vision and an optical power of the outer area to improve near vision when the pupil size is greater than a predetermined size value and the pupil reactivity is less than a predetermined reactivity value.

12. The method of claim 9, further comprising measuring the size of the pupil under a second light condition, and wherein the sizes of the central contact lens area and outer contact lens area are determined according to the size of the pupil under the first light condition and the size of the pupil under the second light condition.

13. The method of claim 9, wherein the position of the central contact lens area is displaced from a center of the contact lens such that the pupil is substantially aligned with the central area under a first focal demand and the pupil is substantially aligned with the outer area under a second focal demand.

14. The method of claim 9, wherein the position of the central contact lens area is displaced from a center of the contact lens such that the pupil is substantially aligned with the central area under a first light condition and the pupil is substantially aligned with the outer area under a second light condition.

15. The method of claim 9, wherein the size of the central area is configured according to a variation in the size of the pupil between a first light condition and a second light condition.

16. The method of claim 9, wherein the size of the central area is configured according to a variation in the size of the pupil between a first focal demand and a second focal demand.

17. The method of claim 9, further comprising measuring a rotational or translational position of a predicate lens on an eye; and wherein the size, shape, and position of the central area is further configured according to the rotational or translational position.

18. A method of patient diagnosis, comprising:
measuring the size of a pupil under a first light condition;
measuring the reactivity of the pupil under a varying light condition or a varying focal demand;
measuring a movement of the pupil under a varying light conditions or a varying focal demand;
determining a size and a position of a central contact lens area and a size and a position of an outer contact lens area according to the measurements;
determining an optical power of the central area to improve near vision and an optical power of the outer area to improve far vision when the pupil size is less than a predetermined size value and the pupil reactivity is greater than a predetermined reactivity value;
determining an optical power of the central area to improve far vision and an optical power of the outer area to improve near vision when the pupil size is greater than a predetermined size value and the pupil reactivity is less than a predetermined reactivity value.

19. The method of claim 18, further comprising: measuring the size of the pupil under a second light condition, and wherein the sizes of the central contact lens area and outer contact lens area are determined according to the size of the pupil under the first light condition and the size of the pupil under the second light condition.

20. The method of claim 19, wherein the position of the central contact lens area is displaced from a center of the contact lens such that the pupil is substantially aligned with the central area under a first focal demand and the pupil is substantially aligned with the outer area under a second focal demand.

21. The contact lens of claim 1, wherein the central area is aspherical.

22. The contact lens of claim 1, wherein the contact lens is a soft lens.

* * * * *

UNITED STATES PATENT AND TRADEMARK OFFICE
CERTIFICATE OF CORRECTION

| | | |
|---|---|---|
| PATENT NO. | : 7,891,810 B2 | Page 1 of 1 |
| APPLICATION NO. | : 12/429113 | |
| DATED | : February 22, 2011 | |
| INVENTOR(S) | : Jerome Legerton | |

It is certified that error appears in the above-identified patent and that said Letters Patent is hereby corrected as shown below:

Title Page; item (73);
Please correct the name of the Assignee on the first Page from "Liguori Management" to
-- Quintex, LLC --.

Signed and Sealed this
Ninth Day of August, 2011

David J. Kappos
*Director of the United States Patent and Trademark Office*